US009681859B2

(12) United States Patent
Muntwyler et al.

(10) Patent No.: US 9,681,859 B2
(45) Date of Patent: Jun. 20, 2017

(54) MAGNETIC NAVIGATION SYSTEM WITH SOFT MAGNETIC CORE ELECTROMAGNETS FOR OPERATION IN THE NON-LINEAR REGIME

(71) Applicant: ETH ZURICH, Zurich (CH)

(72) Inventors: Simon Muntwyler, Zurich (CN);
Bradley Kratochvil, Zurich (CH);
Bradley Nelson, Zumikon (CH);
Dominic Frutiger, Zurich (CH);
Dominik Bell, Zurich (CH); Jonas Baumann, Zurich (CH)

(73) Assignee: ETH ZURICH, Zurich (CH)

( * ) Notice: Subject to any disclaimer, the term of this patent is extended or adjusted under 35 U.S.C. 154(b) by 243 days.

(21) Appl. No.: 14/381,723

(22) PCT Filed: Feb. 26, 2013

(86) PCT No.: PCT/EP2013/000553
§ 371 (c)(1),
(2) Date: Aug. 28, 2014

(87) PCT Pub. No.: WO2013/127516
PCT Pub. Date: Sep. 6, 2013

(65) Prior Publication Data
US 2015/0057676 A1  Feb. 26, 2015

(30) Foreign Application Priority Data
Feb. 28, 2012 (EP) ..................................... 12001304

(51) Int. Cl.
*A61B 17/00* (2006.01)
*A61F 9/007* (2006.01)
(Continued)

(52) U.S. Cl.
CPC ........ *A61B 17/00234* (2013.01); *A61B 34/30* (2016.02); *A61B 34/70* (2016.02);
(Continued)

(58) Field of Classification Search
CPC  A61B 2017/00039; A61B 2017/00137; A61B 2017/00876; A61B 17/00234;
(Continued)

(56) References Cited

U.S. PATENT DOCUMENTS 3,358,676 A    12/1967  Frei et al.
6,311,082 B1   10/2001  Creighton, IV et al.
(Continued)

FOREIGN PATENT DOCUMENTS

CH   WO 2011029592 A1 *  3/2011  ............. A61B 19/22
WO       00/54690 A1      9/2000
(Continued)

OTHER PUBLICATIONS

Robert G McNeil et al.; "Characteristics of an improved magnetic-implant guidance system" in IEEE Transactions on Biomedical Engineering, vol. 42, No. 8, Aug. 1995.
(Continued)

*Primary Examiner* — Christine H Matthews
*Assistant Examiner* — Joshua D Lannu
(74) *Attorney, Agent, or Firm* — Sughrue Mion, PLLC

(57) ABSTRACT

A magnetic manipulation and navigation system for moving a magnetic element through a body comprising at least six electromagnets with soft-magnetic cores arranged in a predetermined position to the body. One or more of the electromagnets operate in the non-linear regime of the magnetization curve of the cores. At least one magnetic field sensor is at one or more predetermined positions outside of the operating region. In the linear region, no feedback is required to set the magnetic field strength. In the non-linear
(Continued)

region, feedback from the magnetic field sensors is used for closed-loop control. The system has an open loop mode operation in the linear regime for fast control signals, for stabilization during displacement of the magnetic element, and a closed-loop operation in the non-linear regime for higher field strengths, to apply forces and moments on the magnetic element while it is in contact with a surface.

18 Claims, 6 Drawing Sheets

(51) Int. Cl.
    *A61B 19/00*     (2006.01)
    *H01F 7/20*     (2006.01)
    *A61B 34/30*     (2016.01)
    *A61B 34/00*     (2016.01)

(52) U.S. Cl.
    CPC .............. *A61F 9/007* (2013.01); *H01F 7/206* (2013.01); *A61B 2017/00039* (2013.01); *A61B 2017/00137* (2013.01); *A61B 2017/00345* (2013.01); *A61B 2017/00876* (2013.01); *A61B 2034/732* (2016.02); *A61B 2034/733* (2016.02)

(58) Field of Classification Search
    CPC .......... A61B 2017/00345; A61B 34/30; A61B 2034/732; A61B 2034/733; A61B 34/70; H01F 7/206; A61F 9/00
    See application file for complete search history.

(56) References Cited

U.S. PATENT DOCUMENTS

2004/0138552 A1    7/2004    Harel et al.
2007/0088197 A1    4/2007    Garibaldi et al.

FOREIGN PATENT DOCUMENTS

WO    2006/137877 A2    12/2006
WO    2011/029592 A1    3/2011

OTHER PUBLICATIONS

Gillies G T et al.; "Magnetic Manipulation Instrumentation for Medical Physics Research" Rev. Sci. Instrum., Mar. 1994; ISSN 0034-6748, pp. 533-562.
Francois Amblard, et al., "A magnetic manipulator for studying local rheology and micromechanical properties of biological systems,", Review of Scientific Instruments, Mar. 1996, pp. 818-827, vol. 67, No. 3.
International Search Report for PCT/EP2013/000553 dated May 10, 2013 [PCT/ISA/210].
Written Opinion for PCT/EP2013/000553 dated May 10, 2013 [PCT/ISA/237].

\* cited by examiner

MAGNETIC NAVIGATION SYSTEM WITH SOFT MAGNETIC CORE ELECTROMAGNETS FOR OPERATION IN THE NON-LINEAR REGIME

TECHNICAL FIELD

The present invention relates to a magnetic manipulation and navigation system for moving a magnetic element through a body comprising at least six electromagnets with soft-magnetic cores arranged in a predetermined position to said body. Such a body usually is a cavity comprising a liquid or soft tissue and a magnetic element to be displaced inside said cavity. This invention allows for the operation of one or more of the electromagnets in the non-linear regime of the magnetization curve of the cores. The system comprises at least one magnetic field sensor at predetermined positions outside of the operating region.

PRIOR ART

WO 2011/029592 discloses a magnetic manipulation system comprising a number of at least six electromagnets with sofa-magnetic cores that are operated in the linear region. The invention is based on the insight, that the precise control of the magnetic element to be displaced in said body space can be achieved when the coils of the electromagnets are controlled in their core's linear regions, i.e. that any change of the strength of the current of any one electromagnetic coil translates into a change of the vector value of the magnetic field according to a linear function of said current and that the change of several currents thus permits to perfect orientation and displacement of the magnetic element within the body.

U.S. Pat. No. 6,311,082 discloses a magnetic manipulation system comprising a number of at least six fixed or manually movable magnets, preferably fixed electromagnets or movable permanent magnets. The document raises the issue that large fixed electromagnets will hamper the use of these elements in connection with an imaging system.

WO 00/54690 relates to a magnetic manipulation system. Said document states that positioning of superconductive electromagnets is difficult when they are employed as stationary coils to guide magnetic elements. WO 00/54690 uses gapped toroid magnets allowing moving a magnetic element within a body by translating the magnets relative to said body. Said magnets are preferably permanent magnets connected by a flux return path. It is also disclosed that the magnets can be electromagnets.

WO 2006/137877 relates to a magnetic manipulation and navigation system for moving a magnetic element through a body using permanent magnets and provides a unit to accurately control the position and orientation of said permanent magnets. Said document mentions that the use of permanent magnets is superior to the use of superconducting magnets comprising superconducting electromagnetic coils.

US 2007/088197 relates to a magnetic navigation system for moving catheters as a magnetic element through a body. The system uses electromagnetic source magnets which might be superconducting or not. The magnetic field is changed by changing the current supplied to the source magnets. The magnetic navigation system according to US 2007/088197 uses a magnetic element having a changeable magnetic moment, i.e. an electromagnet.

The prior art states that electromagnets are difficult to use for such manipulation system, since they have space requirements which usually conflict with the cavity, space or body within which said magnetic element is to be displaced. Additionally such magnets may block the beam path of an imaging system used to follow the movement of the magnetic element.

Francois Amblard, Bernard Yurke, Andrew Pargellis and Stanislas Leibler, "A magnetic manipulator for studying local rheology and micromechanical properties of biological systems", Review of Scientific Instruments, Volume 67, Issue 3, March 1996, pp. 818-827, discloses the use of Hall sensors attached to the face of each of the four coils in a magnetic manipulation system as a feedback to accurately control the currents in each of the coils independently to generate the desired magnetic field magnitude and gradient. This approach was reported to result in a stable and reproducible control of the magnetic field even in spite of the hysteretic effects induced through the use of soft magnetic cores.

Neil Stuart McLagan, "Control of an Electromagnetic Vehicle Suspension", University of Reading, a thesis submitted for the degree of Doctor of Philosophy, 1992; describes the used of either Hall sensors or a search coil wound around the electromagnet poles, close to the pole faces as a feedback for the control of the current in an electromagnetic vehicle suspension.

For accurate magnetic field sensing McLagan proposes that in case of using Hall sensors, they must be placed near the electromagnet pole face to minimise the measurement of leakage flux. Further is suggested to use multiple Hall sensors distributed over the pole face to provide sufficient measurement accuracy even in spite of the non-uniform distribution of flux across the pole face area.

SUMMARY OF THE INVENTION

Based on said prior art it is an object of the invention to provide a magnetic manipulation and navigation system for moving a magnetic element through a body which allows a higher field strength and therefore higher magnetic forces and moments on the magnetic object, while avoiding degradation of the response time.

This object can be achieved by using at least six electromagnets having soft magnetic cores, said magnets being fixed in relation to said body, the control unit supplying the current for the electromagnets, at least one magnetic field sensor at defined locations outside of the operating volume, wherein the system is adapted to allow for an operation in two separate modes, a first open-loop mode operation in the linear regime and a second closed-loop operation in the non-linear regime for higher field strengths.

While during operation in the linear region no feedback is required to set the magnetic field strength, during operation in the non-linear region feedback from the magnetic field sensors is used for closed-loop control. Therefore it is possible to use the faster open-loop operation for the initial way of the magnet in the body volume of the environment whereas upon contact of the magnet with a wall of the environment, the mode is switched into the non-linear regime to apply higher forces.

Current magnetic manipulation systems can only induce relatively small forces and moments onto the magnetic element. The reason for this limitation is that these systems typically involve a linear controller and therefore can only function in the linear regime of a core filled electromagnet. During operation there are phases when higher forces and moments are required, e.g. to achieve a high contact force between the magnetic element and a surface. At higher fields, that are required to induce these higher forces and moments, the core will saturate and the current-field magnitude will become increasingly nonlinear. For this nonlinearity besides the need of a nonlinear control strategy the field generated from multiple coils cannot be predicted using the principle of linear superposition. To accurately predict the magnetic field at least one magnetic field sensing device such as e.g. a hall sensor is introduced into the system, outside the workspace of the magnetic element.

This magnetic field feedback will allow for the accurate control and prediction of the magnetic field even in the highly nonlinear regime above the saturation limit of the soft magnetic cores. Due to this additional feedback the system response times may be reduced. However in applications were large external forces need to be counter-balanced, such as the restoring force of deformed tissue or the drag force while moving in high-viscosity fluid, lower response times are sufficient for stable control.

Besides this magnetic flux feedback a switching methodology is introduced that allows the system to switch between the faster linear control strategy and the nonlinear control required for higher forces and moments. This key functionality ensures no reduction of the system response time at the low field regime (in the linear regime of the soft magnetic cores), while adding the possibility to generate significantly higher forces and moments.

The invention proposes a system and method for applying forces to a soft or permanent magnetic body using a set of electromagnetic coils with soft magnetic cores.

The system can comprise of a series of six or more electromagnetic coils, each having a ferromagnetic core. The control unit supplying the current for the coils is adapted to provide currents to the coils. As opposed to air-core electromagnets according to prior art devices, where the interaction between coils is minimal and can often be neglected, the addition of ferromagnetic cores to the electromagnetic coils according to the invention and their positions in space is explicitly taken into account by the control unit when determining the amount of current to supply to each coil.

The system can apply forces, due to gradients in the magnetic field, and torques, due to the magnetic field alignment on an arbitrary ferromagnetic body within the workspace. This system allows up to five degrees-of-freedom control, three degrees for applying force and two degrees for orienting torques. The electromagnetic coils can be located arbitrarily around the workspace depending on the desired performance of forces and torques exerted on the manipulated object, and the method's explicit control of both the magnetic field's orientation and gradient enables the system to both push and pull on the target body without having to completely surround the workspace.

The system can be controlled manually by an operator using visual or other position feedback in a force controlled paradigm. It is also possible to use a computer system that uses visual or other position feedback for closed-loop positioning control.

The magnetic element, also called microrobot, can move through a large workspace, and is completely unrestrained in the rotation degrees of freedom. This level of wireless control is achieved with a novel electromagnetic system. Whereas magnetic manipulation has typically relied on uniform-field and/or orthogonal systems, which are simple in terms of modelling and control, the present system uses complex non-uniform magnetic fields. The embodiment shown is designed for the control of intraocular microrobots for delicate retinal procedures, but can also be used in other applications or micromanipulation under an optical microscope.

One further application of the invention is in the field of electrophysiology for the control of magnetic ablation catheters. Manipulation of the catheter in the linear regime of the electromagnets allows for fast control signals as they are required for stable magnetic manipulation with translational movement of the catheter tip within the heart chamber to a location at the heart wall where an ablation is done. Once the catheter tip is in contact with the heart wall the system can switch to operate in the non-linear regime in order to increase the field strength with the goal to achieve a higher contact force between the catheter tip and the heart wall, as it is required for good ablation results.

The present invention provides a magnetic manipulation and navigation system for moving a magnetic element through a body comprising at least six electromagnets with soft-magnetic cores arranged in a predetermined position to said body. It allows for the operation of one or more of the electromagnets in the non-linear regime of the magnetization curve of the cores. The system preferably comprises at least one magnetic field sensor at one or more predetermined positions outside of the operating region, e.g. at the tips of the electromagnets. While during operation in the linear region no feedback is required to set the magnetic field strength, during operation in the non-linear region feedback from the magnetic field sensors is used for closed-loop control. The system allows thus for operation in two separate modes, an open-loop mode operation in the linear regime for fast control signals such as they are required for stabilization during displacement of the magnetic element and a closed-loop operation in the non-linear regime for higher field strengths such as they may be required to apply forces and moments on the magnetic element while it is in contact with a surface.

The control unit preferably comprises a calculation module adapted to calculate, for control within the first operating mode the desired current through each of the coils by building a linear set of equations that describe the torque and force, or alternately the field orientation and force, resulting from the current through the coils. This feature can be combined with a further option for the control unit in the second operating mode. Therefore, the control unit can comprise a calculation module adapted to calculate, for control within the second operating mode the desired field through each of the magnetic field sensors by building a linear set of equations that describe the torque and force, or alternately the field orientation and force, resulting from the field at the location of the magnetic field sensors. Furthermore the control unit comprises a feedback controller that will set the currents in each coil in such a manner that the field magnitude and orientation measured at the location of all magnetic field sensors matches the desired value. This has the advantage, that the field sensors are used where the current electromagnet output changes due to heating.

The soft magnetic cores of the electromagnets can have a saturation magnetisation on the order of 1 T, preferably more than 2 T, a coercivity below 1000 A/m, preferably less than 300 A/m.

The control unit preferably is adapted to tune and improve the linear set of equations that describe torque and force, or alternatively the field orientation and force, resulting from the current flowing through the coils, based on the feedback from the magnetic field sensors.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 7. shows a schematic side-view of the magnets having a tapered portion near the target.

DESCRIPTION OF PREFERRED EMBODIMENTS

Figure 1:
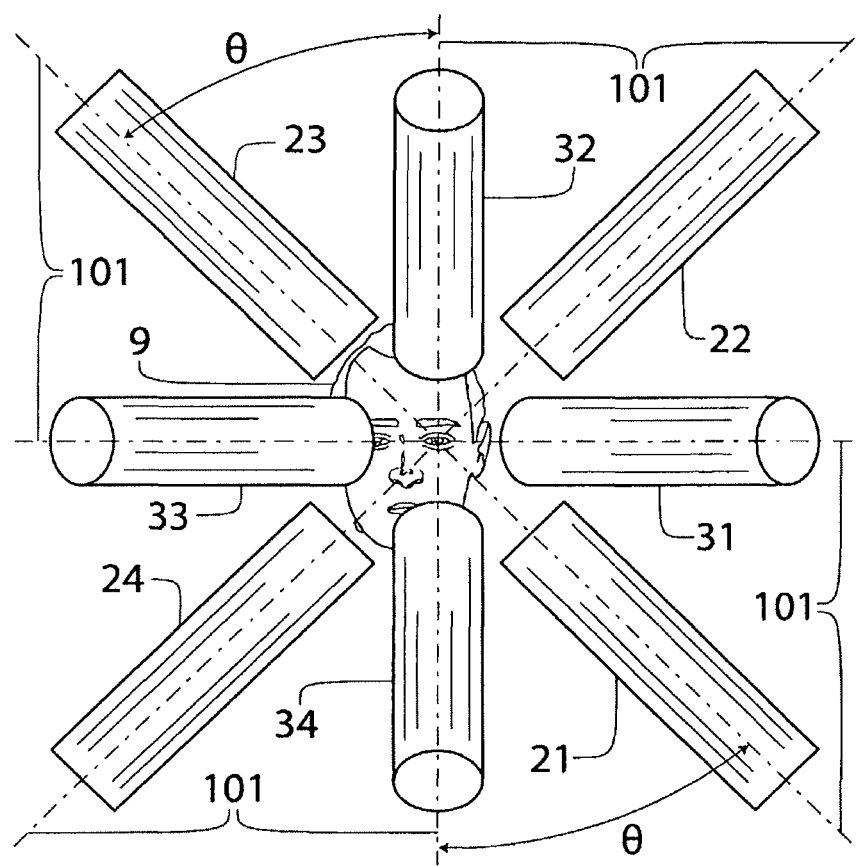
FIG. 1 shows a schematic view from above on the magnets of a system according to the invention.

FIG. 1 shows a schematic view from above on the magnets of a system according to the invention. The system according to the embodiment is arranged for moving a magnetic element (not shown) within an eye. The eye of a person constitutes the body 9 within which the element is to be positioned and displaced. The eye comprises and is a cavity comprising a liquid, constituting the workspace.

The embodiment according to FIG. 1 specifically comprises eight electromagnets fixed in relation to said body. Usually the electromagnets are attached to a fixed frame and the patient, i.e. the body is positioned in relationship to this frame. It might therefore be possible to move the patient during a procedure. Within one embodiment the system has a fixed position with respect to the body whenever the system is in use. Within a different embodiment, the volume containing the magnetic element can be moved without any displacement of the magnetic element, if the system is turned on during the movement. Therefore the electromagnets are arranged in a predetermined position to said body; this may be a fix relationship or there can be a controlled and thus predetermined movement.

There are four electromagnets 21, 22, 23 and 24 being arranged in the drawing plane of FIG. 1, i.e. arranged around the head 9 of a person. The longitudinal axis 101 of the electromagnets 21, 22, 23, 24 intersect at one single point 102, shown in FIG. 2. Said intersection point 102 is in the vicinity of the cavity within which a magnetic element has to be positioned and displaced. In the representation of FIG. 1 this cavity is the eye of a person and therefore the intersection point 102 is near this eye.

Beside the four electromagnets 21, 22, 23 and 24 in the drawing plane of FIG. 1 there are additional four electromagnets 31, 32, 33 and 34 being oriented in an angle of 45 degree in view of the plane of the four electromagnets 21, 22, 23 and 24. The additional four electromagnets 31, 32, 33 and 34 each have a longitudinal axis 101 and the position of the four electromagnets 31, 32, 33 and 34 is such that their longitudinal axis 101 crosses the drawing plane of FIG. 1 at the intersection point 102. In other words, all eight electromagnets 21 to 24 and 31 to 34 are oriented towards the intersection point 102. Although the embodiment shown in FIG. 1 uses eight electromagnets, within another embodiment not shown in the drawings, it is possible to obtain the precise orientation of a magnetic element and its displacement within the cavity using six magnets.

All electromagnets 21 to 24 and 31 to 34 comprise a rod having said axis 101 as symmetry axis and is surrounded by a coil. The electromagnets 21 to 24 are also called the lower set while the electromagnets 31 to 34 above the plane of magnets 21 to 24 are called the upper set.

Figure 2:
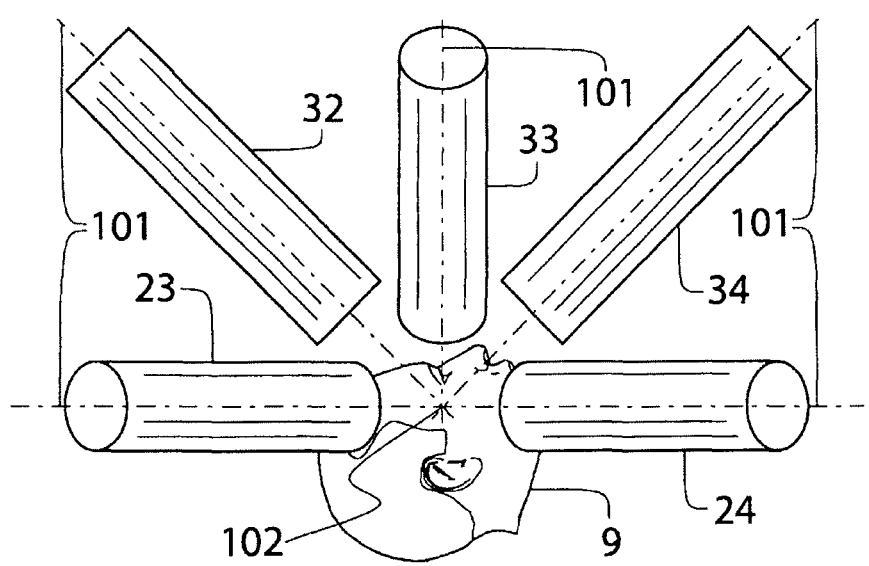
FIG. 2 shows a schematic side-view on the magnets of the system according to FIG. 1.

FIG. 2 shows a schematic side-view on the electromagnets of the system according to FIG. 1. Only electromagnets 23 and 24 are visible from the group of horizontally oriented magnets. Three electromagnets 32, 33 and 34 are visible from the group of inclined oriented magnets, wherein electromagnets 32 and 34 are in the drawing plane.

The typical workspace of a prototype constructed in accordance with the invention was a 25 millimeter diameter sphere, although depending on the magnets chosen different workspaces would be possible. The body 9 of the prototype had a 130 millimeter diameter sphere as open volume between the electromagnets 21, 22, 23 and 24 to allow accommodating e.g. a head of a small animal. The workspace is isotropic with an ability to generate magnetic forces in any direction and any magnetic element pose, e.g. comprising the possibility to levitate the magnetic element against its own weight as well as to provide downward and lateral forces.

Each electromagnet 21 to 24 and 31 to 34 comprises a soft magnetic core; especially a rod of a high-permeability material used to concentrate the magnetic field. Someone skilled in the art can choose such from a wide variety of high-permeability materials which are often ferromagnetic or ferrimagnetic. He can e.g. choose a so called soft magnetic material such as a Fe-50% Co alloy, Permalloy (Ni—Fe), soft iron, iron-silicon alloys, or stainless steel.

The use of soft-magnetic-core electromagnets allows fields that are approximately 20 times stronger over air cores. Air cores would have the advantage that their fields are independent.

The system is capable of performing control of both soft and permanent magnetic bodies. In the case of a hard magnetic body, the magnetic moment is rigidly connected to the frame of the body. With a soft-magnetic body, the magnetic moment is dependent on the applied field and not rigidly connected to the body.

The following describes how the torque and forces induced onto a magnetic body are dependent on the magnetic field and its gradients and starts from the assumption that the magnetic element to be controlled is a magnetized body described by a magnetic moment M in units $A \cdot m^2$. With a permanent magnet, the magnetic moment M is assumed to have a constant magnitude and be rigidly connected to the frame of the body. With a soft-magnetic body, the magnetic moment is dependent on the applied field and cannot be assumed to be rigidly attached to the body. That is, the magnetic moment can rotate with respect to the body and its magnitude can vary greatly with changes in the applied field. In prior work, accurate models for the field-dependent magnetic moment of axially symmetric bodies as shown by J. J. Abbott et al. in "Modeling Magnetic Torque and Force for controlled manipulation of soft-magnetic bodies" were generated. These models include ellipsoids and spheres, as well as assembled-MEMS structures like those used in the present embodiments, for which the modeling was presented by Nagy et al. in "Modeling Assembled-MEMS Microrobots for wireless magnetic control".

The torque on the magnet, in units $N \cdot m$, is expressed as:

$$T = M \times B \qquad (1)$$

where B is the value of the applied magnetic field's flux density at the location of M in units T. It can be found for example in "Permanent Magnet and Electromechanical Devices" by E. P. Furlani. The torque tends to align the magnetic moment with the applied field. In the case of soft-magnetic bodies, the torque tends to align the longest axis of the body (referred to as the easy axis) with the field. It is impossible to apply torque about the axis of M, which is the reason why the goal of the present application is to achieve 5-DOF control rather than 6-DOF control. In soft-magnetic bodies, this means that rotations about the long axis of the body cannot be performed. The skew-symmetric matrix form of a vector to represent vector cross products, M×B=Sk(M)B is used, where $$Sk(M) = Sk\left(\begin{bmatrix} m_x \\ m_y \\ m_z \end{bmatrix}\right) = \begin{bmatrix} 0 & -m_z & m_y \\ m_z & 0 & -m_x \\ -m_y & m_x & 0 \end{bmatrix} \quad (2)$$

where x, y, and z explicitly refer to the basis directions of the world frame in which all vectors are expressed. The force on the magnetic moment, in units N, is expressed as $$F=(M\cdot\nabla)B \quad (3)$$

Since there is no electric current flowing through the region occupied by the body, Maxwell's equations provide the constraint ∇×B=0. This allows expressing (3), after some manipulation, in a more intuitive form:

$$F = \begin{bmatrix} \frac{\partial B}{\partial x} & \frac{\partial B}{\partial y} & \frac{\partial B}{\partial z} \end{bmatrix}^T M \quad (4)$$

Note that the applied magnetic field as H in units A/m can be described with $B=\mu_0 H$ and $\mu_0 = 4\pi 10^{-7}$ T·m/A.

The forces and torques acting on a magnetic body depends on the magnetic field and thus precise knowledge of the magnetic field present at any time and at any location in the workspace is required for a stable control of the magnetic body.

Within a given static arrangement of electromagnets, each electromagnet creates a magnetic field throughout the workspace. In the case of air-core electromagnets the field contributions of the individual electromagnets can be computed individually and linearly superimposed to determine the field at any location in the workspace. When the electromagnets have soft-magnetic cores, the field contributions of the individual electromagnets are no longer decoupled (problem A) and more importantly not strictly linear dependent on the applied currents (problem B).

To account for the magnetic field induced in neighbouring electromagnets (problem A), the field contribution of a given electromagnet is calculated in situ. This calculation can be derived from a variety of methods such as measuring the field generated by a reference current through an individual coil throughout the workspace and interpolating the field at a desired location, through the use of finite element analysis of the system, mathematically modelling the various cores and their interactions, or other methods familiar to one versed in the state-of-the-art. The method as disclosed in WO 2011/029592 can be used for this first operating mode.

Figure 3:
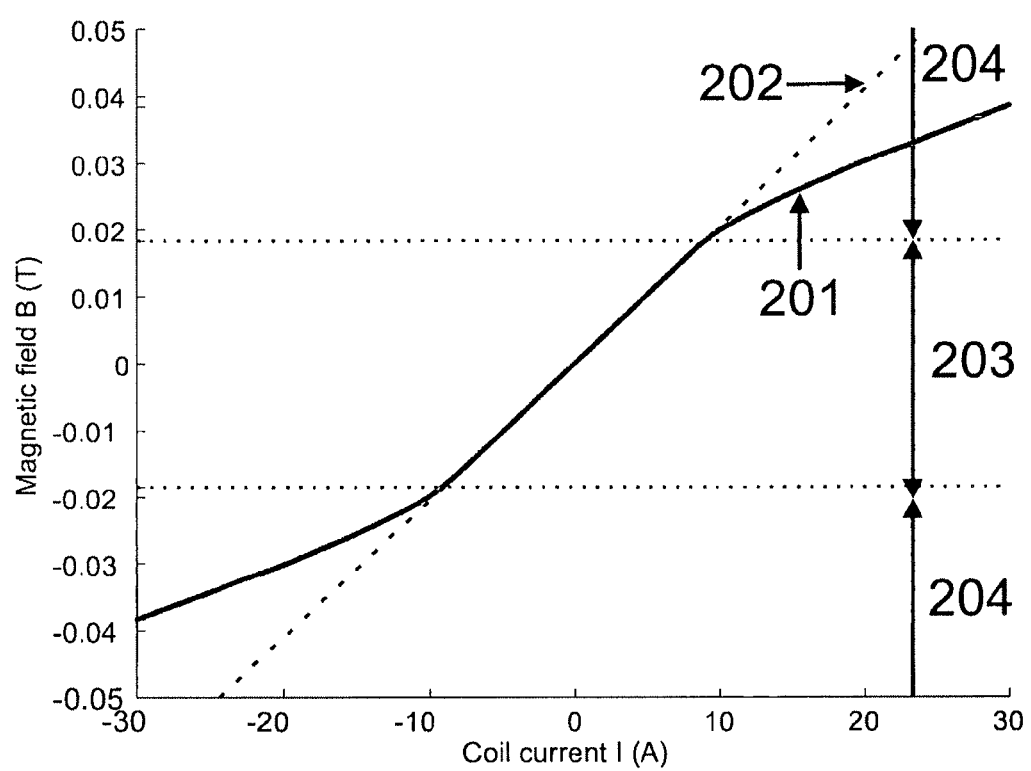
FIG. 3 shows an example of the current-field relationship generated by a single electromagnet with soft-magnetic core.

The reason for a nonlinear dependence (problem B) of the magnetic field to the current originates from the magnetic properties of the soft magnetic cores. In FIG. 3 a typical curve of the current-field relationship, of an electromagnet with soft magnetic core, indicated by 201 is shown (as the case in the prototype constructed in accordance with the invention).

Two general states of the magnetic manipulation system are distinguished. The first operating mode applies to the "linear state", indicated by 203 in FIG. 3, wherein the magnetic field of each of the electromagnets is strictly linear dependent on the applied current. The second operating mode is applied to the "non linear regime", which contains both, the region indicated by 203 and 204 in FIG. 3. In the region indicated by 204, the soft magnetic core is saturated and therefore cannot amplify the magnetic field any more (compared to the region indicated by 203), it only grows (in absolute terms) in a linear differential relationship to the supplemental current. Therefore, to operate the system in the entire region indicated by 203 and 204, a new control strategy for the second operating mode is applied, dealing with this nonlinear dependence.

In other words, in order to ensure a correct prediction and control of the generated magnetic field and gradients, two different control strategies are used. A linear control, preferably without a feedback-loop, is used as first operating mode, when all the electromagnets are operated in their linear regime 203 and a nonlinear strategy is used in the second operating mode, when at least one electromagnet is getting saturated and requires to be operated in the higher field regime 204, using a closed-loop control.

The force and torques induced in the magnetic body are proportional to the field magnitude and gradient. Therefore, when using higher fields, higher forces and torques can be achieved. As can be seen in FIG. 3, generating the highest possible fields will result in operating the system in the nonlinear regime. Therefore, at low forces and torques, the system can operate in the linear regime, but as higher forces and torques are required, the system needs to switch the control strategy since it needs to be operated in the nonlinear regime.

For the operation of the system in the "linear regime", the cores are chosen with minimal hysteresis and the system is operated in the cores' linear magnetization region indicated by 203 in FIG. 3, i.e. linearity around the current value 0 Ampere, which enables the control unit to implement the assumption that the field contributions of the individual currents superimpose linearly. The control unit calculates the desired current through each of the coils by building a linear set of equations dependent on current that describe the torque and force, or alternately the field orientation and force, on the modelled soft or hard-magnetic body. Using linear algebra, the current through each coil is able to be found by techniques such as the pseudoinverse or similar mathematical tools. Depending on the availability of closed-loop feedback, the field can either be calculated at the location of the magnetic body to be controlled, or if the magnetic field does not vary greatly across the workspace, it may be calculated at the centre of the workspace.

Figure 4:
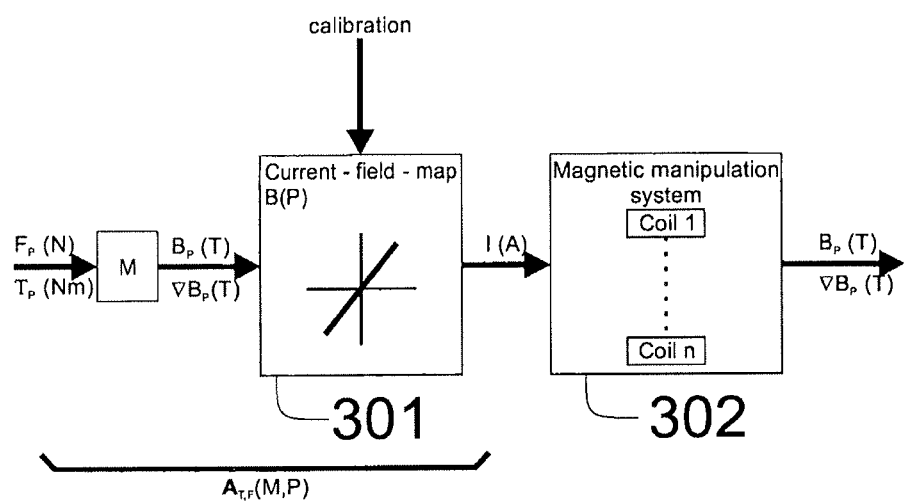
FIG. 4 shows the control strategy for the linear regime.
Figure 5:
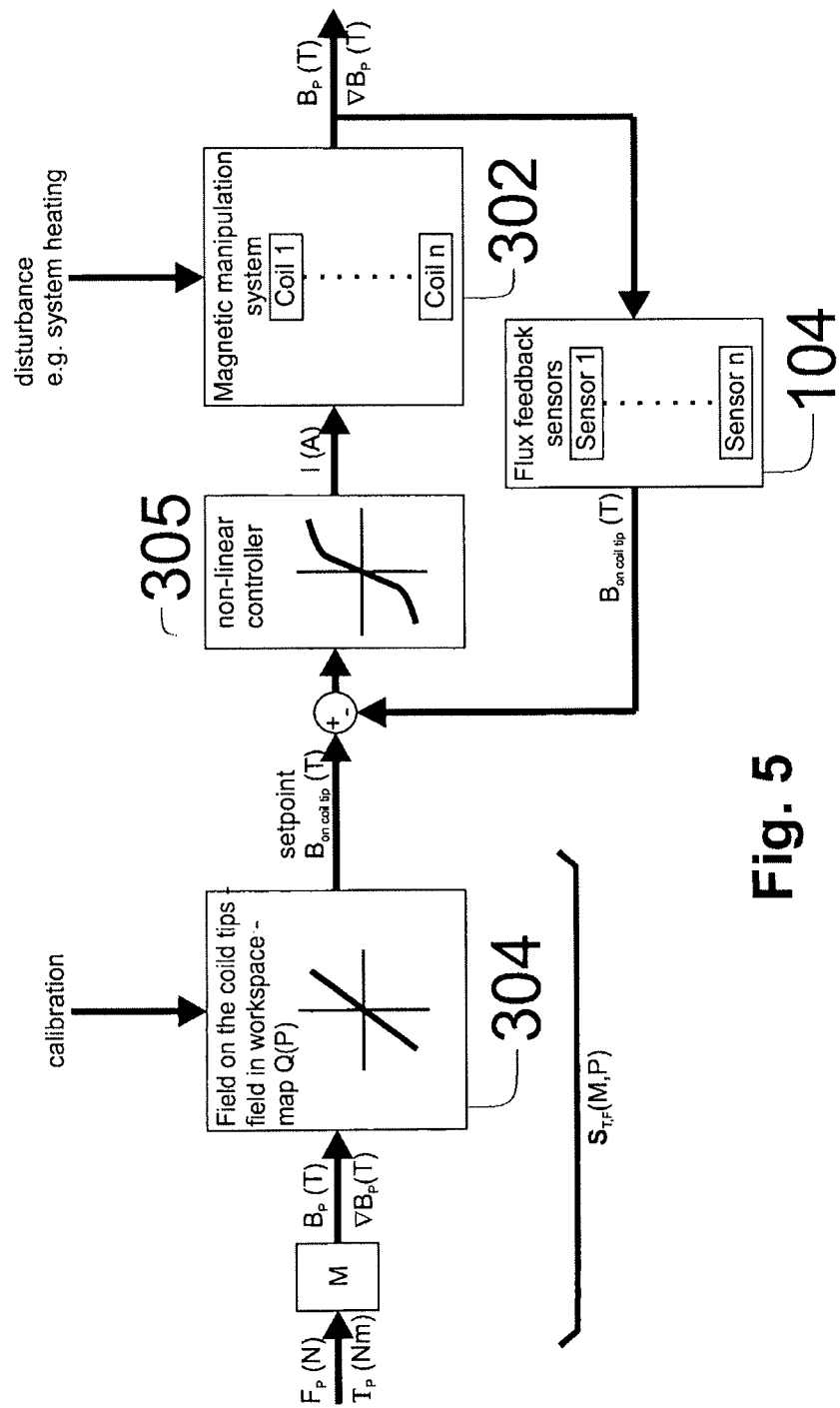
FIG. 5 shows the control strategy for the non-linear regime.

In the following first the control strategy for the linear regime is described, when the device is working in the first operating mode, followed by the description of the adaptations necessary to operate the system in the nonlinear regime. An overview of the principle changes when switching between the two strategies is shown in FIG. 4 and FIG. 5.

Within a given static arrangement of electromagnets operated in their "linear regime", each electromagnet creates a magnetic field throughout the workspace that can be precomputed, from the current-field maps. Due to the linear characteristic of the system only knowledge of the unit-current field maps is required within the first operating mode.

There are a number of potential methods to generate the unit-current field maps. Either the magnetic field of the final system can be explicitly measured at a grid of points or the field values can be computed at the grid of points using FEM models. In either case, trilinear interpolation is used during real-time control. For each of the electromagnets, a unit-current field map has to be calculated, but it is possible to calculate fewer maps, and then rotate them during run time using homogeneous transformations. Potentially electromagnets of different geometry and size at different distances from the centre could be used which would require the calculation of the unit-current field map for each of the electromagnets individually. To generate the unit-current gradient maps using either method, either the gradient is explicitly measured/modeled at the grid of points, or the field data is numerically differentiated, so care must be taken to minimize noise in the field map. An alternative to the trilinear-interpolation approach is to fit a continuous function to the field. This is the approach that is used here. The analytical field model also has a simple analytical derivative. These analytical models are used to build the unit-current field and gradient maps during run time.

Based on these unit-current fields, at any given point in the workspace P, the magnetic field due to a given electromagnet can be expressed by the vector, whose magnitude, as long as the system is in the "linear regime", varies linearly with the current through the electromagnet, and as such can be described as a unit-current vector in units T/A multiplied by a scalar current value in units A:

$$B_e(P) = \tilde{B}_e(P) i_e \quad (5)$$

The subscript e represents the contribution due to the $e^{th}$ electromagnet. The field $B_e$ (P) is the field due to the current flowing through electromagnet e and due to the soft-magnetic cores of every electromagnet. With air-core electromagnets, the individual field contributions are decoupled, and the fields can be individually precomputed and then linearly superimposed. This is not the case with soft-magnetic-core electromagnets; so that the field contributions of a given electromagnet are to be precomputed in situ. However, if an ideal soft-magnetic material with negligible hysteresis is assumed, and the system operates with the cores in their linear magnetization region, and it can still be assumed that the field contributions of the individual currents (each of which affect the magnetization of every core) superimpose linearly. Thus, it is assumed that the magnetic field at a point in the workspace is simply the sum of the contributions of the individual currents:

$$B(P) = \sum_{e=1}^{n} B_e(P) = \sum_{e=1}^{n} \tilde{B}_e(P) i_e \quad (6)$$

This assumption is clearly also valid for air-core electromagnets. This linear summation of fields can be expressed as:

$$B(P) = [\tilde{B}_1(P) \quad \ldots \quad \tilde{B}_n(P)] \begin{bmatrix} i_1 \\ \vdots \\ i_n \end{bmatrix} = [B(P)]I \quad (7)$$

The [B(P)] matrix is known at each point in the workspace and can be calculated online, or calculated offline and then interpolated. It is also possible to express the derivative of the field in a given direction in a specific frame, for example the x direction, as the contributions from each of the currents:

$$\frac{\partial B(P)}{\partial x} = \left[ \frac{\partial \tilde{B}_1(P)}{\partial x} \quad \ldots \quad \frac{\partial \tilde{B}_n(P)}{\partial x} \right] \begin{bmatrix} i_1 \\ \vdots \\ i_n \end{bmatrix} = [B_x(P)]I \quad (8)$$

Considering (1) and (4), the magnetic torque and force on the microrobot (i.e. the magnetic element) can be expressed as $$\begin{bmatrix} T \\ F \end{bmatrix} = \begin{bmatrix} Sk(M)[B(P)] \\ M^T[B_x(P)] \\ M^T[B_y(P)] \\ M^T[B_z(P)] \end{bmatrix} \begin{bmatrix} i_1 \\ \vdots \\ i_n \end{bmatrix} = [A_{T,F}(M,P)]I \quad (9)$$

That is, for each microrobot pose, the n electromagnet currents are mapped to a torque and force through a 6×n actuation matrix $[A_{TF}$ (M, P)]. For a desired torque/force vector, the choice of currents that gets us closest to the desired torque/force value can be found using the pseudoinverse presented by R. A. Horn et al. in "Matrix Analysis":

$$I = [A_{T,F}(M,P)]^{-1} \begin{bmatrix} T_{des} \\ F_{des} \end{bmatrix} \quad (10)$$

Nota Bene: The use of (9) requires knowledge of the microrobot's pose and magnetic moment. If there are multiple solutions to achieve the desired torque/force, the pseudoinverse finds the solution that minimizes the 2-norm of the current vector, which is desirable for the minimization of both energy consumption and heat generation. The pseudoinverse of [A] makes use of the singular value decomposition $[A]=U\Sigma V^T$, where $\Sigma$ is the 6×n singular-value matrix, where the left-most 6×6 elements form a diagonal matrix of the six ordered singular values $\sigma_i$, U is the 6×6 orthonormal matrix whose columns are the six output singular vectors, and V is the n×n orthonormal matrix whose columns are the n input singular vectors. The pseudoinverse is computed as $[A]^{-1}=U\Sigma^{-1}V^T$, where $\Sigma^{-1}$ is an n×6 matrix, where the upper-most 6×6 elements form a diagonal matrix with the $j^{th}$ diagonal element defined as $$\frac{1}{\sigma_j}$$

if $\sigma_j \neq 0$ and as 0 if $\sigma_j=0$, and all other entries equal 0, see Horn et al. The sixth singular value will always be $\sigma_6=0$ and the sixth column of U will always be $$U_6=[0\ 0\ 1\ 0\ 0\ 0]^T \quad (11)$$

corresponding to torque generation about the magnetization axis, which is never possible. It is required that the other five singular values are nonzero for full 5-DOF control.

In the case of a microrobot moving through fluid, where the microrobot can align with the applied field unimpeded, and a modified control strategy can be used. Rather than explicitly controlling the torque, the magnetic field can be controlled to the desired orientation, to which the microrobot will naturally align, and then the force on the microrobot is controlled explicitly:

$$\begin{bmatrix} B \\ F \end{bmatrix} = \begin{bmatrix} [B(P)] \\ M^T[B_x(P)] \\ M^T[B_y(P)] \\ M^T[B_z(P)] \end{bmatrix} \begin{bmatrix} i_1 \\ \vdots \\ i_n \end{bmatrix} = [A_{B,F}(M,P)]I \quad (12)$$

Then the currents I is set as $$I = [A_{B,F}(M,P)]^{-1} \begin{bmatrix} B_{des} \\ F_{des} \end{bmatrix} \quad (13)$$

Full 5-DOF control, which required a rank-5 actuation matrix in (9), corresponds to a rank-6 actuation matrix in (12). As with (9), the use of (12) requires knowledge of the microrobot's pose and magnetic moment. However, in this case the microrobot will align with the applied field under open-loop control. If it is ensured that the direction of B does not change too rapidly, it is reasonable to assume that M is always aligned with B, which means that there is no need to measure the microrobot's full pose explicitly, but rather, the magnitude of M is to be estimated and the microrobot's position P is to be measured. In addition, if a magnetic field, especially within the first operating mode, should be generated that does not vary greatly across the workspace, so that it is reasonable to assume that the microrobot is always located at P=0 for purposes of control, eliminating the need for any localization of the microrobot.

In the cases where high forces or torques are required, the system needs to generate higher fields and therefore needs to be operated in the second operating mode, i.e. in a nonlinear regime. High forces or torques are required in cases such as when the magnetic body is required to push against elastic tissue with a high stiffness or move through a fluid with a high viscosity.

Now, in the nonlinear regime, the field at any location in the workspace P cannot be calculated simply by using the pseudoinverse of the actuation matrix $[A_{T,F}(M,P)]$, which is calculated form the unit-current field maps and the magnetic moment M as indicated in FIG. 4. For the operation of the system in the "nonlinear regime" the relationship between the applied current and the resulting magnetic field is not linear any more, such as indicated in FIG. 3. Due to this nonlinearity the field at any current combination and any location in the workspace cannot be calculated based on the linear superimposing and linear extrapolation of the unit-current field maps. Therefore, in the "nonlinear regime" a new control strategy, such as shown in FIG. 5 is applied.

The basic idea of the nonlinear control strategy of the magnetic system according to the second operating mode is to identify the part of the system that introduces the nonlinearity and take control of it using an additional sensor and a nonlinear controller. In the case of the magnetic manipulation system, the soft magnetic cores of the coils will saturate at a certain magnetic field magnitude and thus not further amplify the magnetic field. At this point the current-field relationship will become nonlinear and with that also the current-field map relationship. Since a feedback sensor at any location P in the workspace is not possible, it is highly desired to ensure, that these field maps can still be described using a linear approach.

To overcome the problem induced by the nonlinear relationship between the current running through each coil and the generated magnetic field, at least one, preferably more than one additional sensor to measure the magnetic field, such as hall sensors are introduced into the system at multiple locations outside of the workspace. Different locations and numbers of these feedback sensors can be used. In this embodiment the positioning of one or multiple hall sensors 104 at the tip of each electromagnet, facing the workspace as shown in FIG. 6 is demonstrated.

By introducing a magnetic field sensing sensor 104 at the tip of each core the input as well as the output of the nonlinear part of the system (the coils with the soft magnetic cores) is known. This configuration allow for controlling the field at the tip of each coil using a nonlinear controller as shown in FIG. 5 without the knowledge of the currents and exact characteristic of the coils.

This nonlinear feedback control strategy has a number of benefits. Besides the fact that it can induce much higher forces and torques onto the magnetic body, other imperfections in the system, such as hysteresis, nonlinearities or system heating, which will induce significant errors in the prediction or control of the magnetic field, are measured and compensated by this feedback control.

Figure 6:
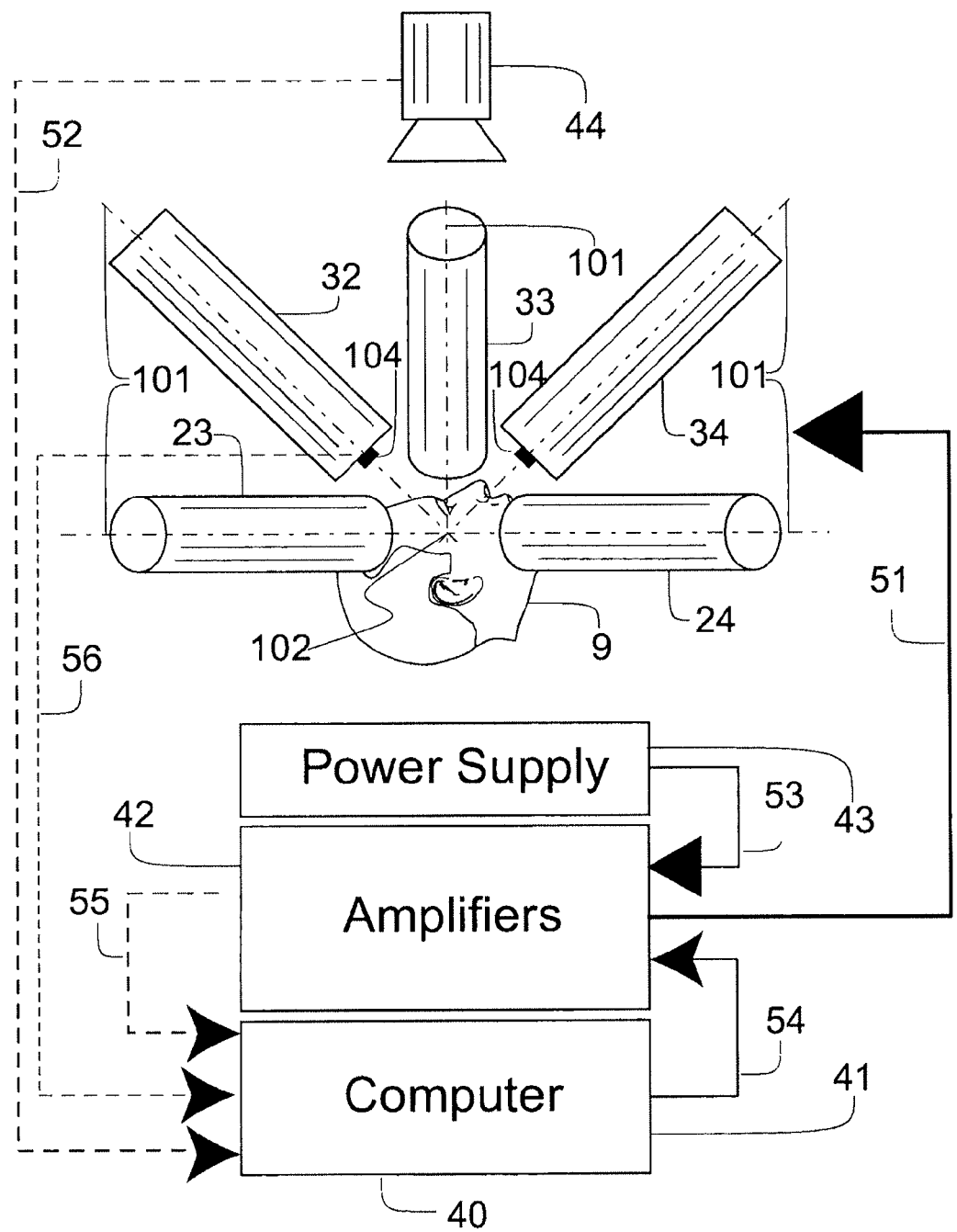
FIG. 6 shows a schematic side-view on the system according to FIG. 1 including a control unit and field sensors.

In this embodiment, one hall sensor is placed at the tip of each electromagnet (facing the workspace), located in the centerline, indicated by 101 in FIG. 6. In this configuration the output of each hall sensor can be dominantly related to the field generated by the corresponding coil. During the earlier discussed generation of the unit-current field maps, used for the control strategy in the linear regime, also the hall sensor outputs are recorded. Since the relationship between the field at the tip of the cores and the field at any location in the workspace P is linear, the linear relationship Q(P) can be calculated for each point in the workspace.

What in the linear control strategy where the "unit-current-field maps" are now the "field on the core-field in the workspace-maps". Due to their linearity the principle of linear extrapolation and superimposing can be applied.

Q(P) can own be used to predict or control the field at any location in the workspace P as described by (14), where B(P) is the field at the location of interest P in the workspace and $H=[H_1, \ldots, H_n]^T$ are the readings of the n Hall sensors.

$$B(P) = [Q_1(P) \ldots Q_n(P)] \begin{bmatrix} H_1 \\ \vdots \\ H_n \end{bmatrix} = Q(P)H \quad (14)$$

As the case for the linear regime, the derivative can be expressed as in (15) which is necessary to predict and control the force.

$$\frac{\partial B(P)}{\partial x} = \begin{bmatrix} \frac{\partial Q_1(P)}{\partial x} & \ldots & \frac{\partial Q_n(P)}{\partial x} \end{bmatrix} \begin{bmatrix} H_1 \\ \vdots \\ H_n \end{bmatrix} = Q_x(P)H \quad (15)$$

In the nonlinear regime a nonlinear feedback controller is used to control the current running through each coil in such a way, that the fields at the tip of the coils will reach the desired values. The mapping from the field at the electromagnet tips to the field at any location in the workspace P is done using Q(P).

Similar as in the linear control, using the magnetic moment M, the relationship can be extended to incorporate the forces and torques. Here, in the nonlinear control strategy, the currents are not used, since they are controlled in the nonlinear feedback controller. In this case the actuation matrix describes the relationship between the hall sensor readings and the forces and torques acting on the magnetic body. Given a suitable nonlinear feedback controller is used, the desired Hall sensor reading is equal to the actual reading.

For the nonlinear control strategy the actuation matrix S is described in (16) or (17) respectively.

$$\begin{bmatrix} T \\ F \end{bmatrix} = \begin{bmatrix} Sk(M)[Q(P)] \\ M^T[Q_x(P)] \\ M^T[Q_y(P)] \\ M^T[Q_z(P)] \end{bmatrix} \begin{bmatrix} H_1 \\ \vdots \\ H_n \end{bmatrix} = [S_{T,F}(M, P)]H \quad (16)$$

$$\begin{bmatrix} B \\ F \end{bmatrix} = \begin{bmatrix} [Q(P)] \\ M^T[Q_x(P)] \\ M^T[Q_y(P)] \\ M^T[Q_z(P)] \end{bmatrix} \begin{bmatrix} H_1 \\ \vdots \\ H_n \end{bmatrix} = [Q_{B,F}(M, P)]H \quad (17)$$

The control system proposed in the description of this embodiment is quite simple, but it overcomes problems of the prior art.

Using a system only in its linear regime allows for a relatively simple control strategy enabling fast and robust control of the magnetic body. As a drawback, the system is limited to relatively low forces and toques. As higher force or torques are required, the proposed controller will switch into the nonlinear control strategy, where multiple flux feedback sensors are used to measure the field generated by the magnetic system and a nonlinear feedback controller will autonomously control the current in each coil to generate the desired fields in the second operating mode.

Two main features are introduced within the two different operation modes. Through the introduction of magnetic flux feedback sensors a control strategy has been developed, that will allow for the operation of a magnetic manipulation system with soft magnetic core, to operate above its saturation limit to generate much larger forces and torques. Secondly a switching between the linear and nonlinear control strategy is proposed. This will ensure the optimal system performance for each regime. In the linear regime due to the simple control strategy a fast control of the magnetic body can be achieved, and in the nonlinear regime higher force and torques can be achieved. Therefore any magnetic element to be manipulated can be moved quickly to the point of interaction and possible problems as passing difficult zones with wall contact of the fluid container can be overcome through switching in the slower but more powerful second control mode.

Due to the feedback control of the applied current, the overall bandwidth of the magnetic manipulation system will decrease. However, only higher forces are required when the magnetic body is e.g. pushed against an elastic tissue or moved through a fluid with a very high viscosity, and therefore, this decrease in system bandwidth will not affect the overall performance of the control of the magnetic body. The main reason for this originates, from the fact that as the viscosity of the fluid surrounding the magnetic body increases or the magnetic body is connected to a tissue, its movement are also damped and a control strategy at a lower bandwidth can be accepted.

Someone skilled in the art can choose different implementations of the current control schemes in the control unit 40. The common point is that the control unit 40 is to be adapted to operate the electromagnetic coils of each of the electromagnets 21-24 and 31-34 to achieve either the desired field on the coil tip (nonlinear regime) or the desired currents (linear regime).

Said electromagnets 21 to 24 and 31 to 34 are connected to a control unit 40 consisting of a computer 41, amplifiers 42, and power supply 43 as shown in FIG. 6 supplying the current to the coils 12 of the electromagnets. The amplifiers 42 comprise preferably one amplifier for each electromagnet. These amplifiers are connected with the corresponding electromagnet with a supply line 51. At least one camera 44, preferably two cameras, is/are positioned to acquire an image of the magnetic element in the body 9. The camera is a visualization unit or can be named—in connection with the corresponding control unit—as a localization unit. The corresponding signals are transmitted with the optic signal connection 52 to the computer 41 of the control unit 40 additionally the ridings form the flux feedback sensor 104 are transmitted through the flux feedback sensor connection to the computer as well. The computer 41 generates control signals for each amplifier which are transmitted with the control connection 54 to the amplifier unit 42 which is connected with the power supply 43 using a power supply connection 53 and with the computer 41 with an additional status connection 55 to allow the control unit 40 to take into the control any changes in the amplifier regime.

In order to achieve the control or to allow an open loop positioning of the magnetic element/microrobot, the device is undergoing a calibration method as explained above. Every single one of the plurality of electromagnets is supplied (one after the other) with a specific current and the effect in situ in a predetermined space (i.e. the body) is determined. This determination can be a calculation or a measurement.

FIG. 7 shows a schematic side-view on the magnets of a system according to an embodiment of the invention that permits a greater concentration of coils near a central work space. There are plural electromagnets 61, 62, 63, 71, 72 arranged at an angle about a perpendicular symmetry axis. The coils have a compact concentration with regard to workspace 3. This concentration is facilitated by modifying the electromagnets of FIGS. 1 and 2 such that the core 11 of each magnet can be positioned nearer to the central workspace 3 of the device. The electromagnet has a bare core 83, a tapered or broadening coil portion 82 ending at a cylindrical coil portion 81. The bare core part 83 can have a length of about the radius of the core itself.

LIST OF REFERENCE SIGNS

| | |
|---|---|
| 9 | body |
| 21-24 | four electromagnets in a plane |
| 31-34 | four inclined electromagnets |
| 40 | control unit |
| 41 | computer |
| 42 | amplifier |
| 43 | power supply |
| 44 | camera assembly |
| 51 | supply line |
| 52 | optic signal connection |

-continued

LIST OF REFERENCE SIGNS

| | |
|---|---|
| 53 | power supply connection |
| 54 | control connection |
| 55 | status connection |
| 56 | flux feedback sensor connection |
| 101 | longitudinal axis |
| 102 | intersection point |
| 104 | magnetic flux feedback sensors |
| 201 | current field relationship |
| 202 | linear approximation in the linear regime |
| 203 | linear regime |
| 204 | nonlinear regime |
| 301 | current-field-map A(P) |
| 302 | magnetic manipulation system |
| 304 | field on the coil tip - field on in the workspace - map Q(P) |
| 305 | nonlinear controller |

The invention claimed is:

1. A magnetic manipulation and navigation system for moving a magnetic element through a body comprising:
at least six electromagnets fixed in predetermined relation to said body; and
a control unit supplying current for the electromagnets,
wherein the electromagnets have electromagnetic coils and soft magnetic cores,
wherein the soft magnetic cores each have a magnetization curve comprising a central linear region and a non-linear region,
wherein the control unit comprises a first operating mode and a second operating mode,
wherein in the first operating mode, the current supplied by the control unit to each of the electromagnets is configured to operate the electromagnetic coils of each of the electromagnets in the central linear region of the magnetization curve of respective cores as a linear regime,
wherein in the second operating mode, the current supplied by the control unit to each of the electromagnets is configured to operate the electromagnetic coils of one or more of the electromagnets in the non-linear region of the magnetization curve of the respective cores as a non-linear regime, and
wherein the first operating mode is an open-loop mode operation in the linear regime and the second operating mode is a closed-loop operation in the non-linear regime.

2. The system according to claim 1, comprising at least one magnetic field sensor at a predetermined position outside of a navigating region of the magnetic element through the body,
wherein during operation in the first operating mode the control unit controls the current in absence of a feedback signal, and
wherein during operation in the second operating mode the control unit controls the current using feedback from the at least one magnetic field sensor for closed-loop control.

3. The system according to claim 2, wherein the control unit is configured to switch from the first operating mode to the second operating mode upon reception of a sensor signal from the magnetic field sensor and relating to the magnetic element.

4. The system according to claim 1, wherein each electromagnet has a negative and a positive saturation value of flux density, wherein the central linear regions of the electromagnets are delimited by the negative and positive saturation values of the flux density of each electromagnet being in an interval between the negative and positive saturation value of each electromagnet, delimited at a threshold value of the negative and positive saturation value of each electromagnet chosen from the group of threshold values at 70%, 80% or 90%.

5. The system according to claim 4, wherein the soft magnetic cores of the electromagnets have a saturation magnetisation of more than 1 T, and a coercivity below 1000 A/m.

6. The system according to claim 5, wherein the soft magnetic cores of the electromagnets have a saturation magnetisation of more than 2 T, and a coercivity less than 300 A/m.

7. The system according to claim 1, wherein each electromagnet has an aspect ratio of width to length, and
wherein the aspect ratio of width to length of each electromagnet is between 4 and 10.

8. The system according to claim 1, wherein the magnetic element has a position and orientation inside the body, and
wherein the control unit is connected to a localization unit, configured to detect the position and orientation of the magnetic element inside the body.

9. The system according to claim 8, wherein the localization unit has an output signal, wherein the output signal of said localization unit is connected to a closed-loop module of the control unit for use within the second operating mode.

10. The system according to claim 1, wherein the at least six electromagnets are eight electromagnets,
wherein a first group of four electromagnets of the eight electromagnets is arranged approximately in a plane, each of the electromagnets of said first group having an angular distance of between 80 to 100 degrees one from another,
wherein a second group of four electromagnets of the eight electromagnets are all inclined in an angle of between 35 to 55 degrees against the plane of the first group, each of the electromagnets of said second group having an angular distance of between 80 to 100 degrees one from another, and
wherein the electromagnets of said first group and said second group are regularly spaced at between 35 to 55 degrees, one from another.

11. The system according to claim 1, wherein the at least six electromagnets are six electromagnets,
wherein a first group of three electromagnets of the six electromagnets is arranged approximately in a plane, each of the electromagnets of said first group having an angular distance of between 110 to 130 degrees one from another,
wherein a second group of three electromagnets of the six electromagnets are all inclined in an angle of between 35 to 55 degrees against the plane of the first group, each of the electromagnets of said second group having an angular distance of between 110 to 130 degrees, one from another, and
wherein the electromagnets of said first group and said second group are regularly spaced at between 50 to 70 degrees one from another.

12. The system according to claim 1, wherein the at least six electromagnets are six electromagnets,
wherein a first group of three electromagnets of the six electromagnets is arranged below a plane, all inclined in an angle of between 35 to 55 degrees against said plane, and all having an angular distance of between 110 to 130 degrees one from another in view of said plane, wherein a second group of three electromagnets of the six electromagnets are all inclined in an angle of between 35 to 55 degrees against said plane opposite to the first group, each of the electromagnets of said second group having an angular distance of between 110 to 130 degrees one from another, wherein the electromagnets of the first group and the second group are regularly spaced at between 50 to 70 degrees one from another.

13. The system according to claim 1, wherein the at least six electromagnets are eight electromagnets, wherein a first group of four electromagnets of the eight electromagnets is arranged above a plane, all inclined in an angle of between 20 to 40 degrees against said plane, and all having an angular distance of between 80 to 100 degrees one from another in view of said plane, wherein a second group of four electromagnets of the eight electromagnets are arranged above said plane, all inclined in an angle of between 35 to 55 degrees against said plane, each of the electromagnets of said second group having an angular distance of between 80 to 100 degrees one from another, wherein the electromagnets of the-said first group and the-said second group are regularly spaced at between 40 to 50 degrees one from another.

14. The system according to claim 1, wherein the control unit is configured to provide a calibration mode, within which every single one of the electromagnets is supplied one after the other with a predetermined current and a magnetic field sensor senses an effect in situ in said body;

wherein a resulting magnetic field within said body upon supply of said predetermined current to all said electromagnets is determined, and wherein the control unit generates control signals for the electromagnets in the linear region around said predetermined current for use in the first operation mode.

15. The system according to claim 1, wherein a portion of each core of the electromagnets directed towards the workspace body is bare for a length equivalent to the radius of each core, followed by a tapered coil arrangement until a cylindrical coil arrangement encompassing a remainder of each core.

16. A magnetic manipulation and navigation system for moving a magnetic element through a body comprising:

at least six electromagnets fixed in predetermined relation to said body, a control unit supplying current for the electromagnets, and a plurality of magnetic field sensors, wherein each magnetic field sensor is associated to one of the electromagnets and is configured to measure field magnitude and orientation of said electromagnet, wherein the electromagnets have electromagnetic coils and soft magnetic cores, wherein the soft magnetic cores each have a magnetization curve comprising a central Linear region and a non-linear region, wherein the control unit comprises a first operating mode and a second operating mode, wherein in the first operating mode, current supplied by the control unit to each of the electromagnets is configured to operate the electromagnetic coils of each of the electromagnets in the central linear region of the magnetization curve of respective cores as a linear regime, wherein in the second operating mode, current supplied by the control unit to each of the electromagnets is configured to operate the electromagnetic coils of one or more of the electromagnets in the non-linear region of the magnetization curve of respective cores as a non-linear regime, wherein the control unit comprises a calculation module configured to calculate for control within the first operating mode a value of current through each of the coils by building a linear set of equations describing either torque and force or alternately field orientation and force resulting from current flow through the coils, and to calculate for control within the second operating mode a value of field through each of the magnetic field sensors by building a linear set of equations describing torque and force or alternately field orientation and force resulting from the field at the location of the magnetic field sensors, and wherein the control unit comprises a feedback controller that will set the currents in each coil in such a manner that the field magnitude and orientation measured at the location of associated magnetic field sensors match the calculated field value.

17. The system according to claim 16, wherein the calculation module comprises a pseudoinverse or equivalent least squares solution of the linear set of equations to calculate a desired current in each of the electromagnets for a given desired torque and force, or alternately for a given desired field orientation and force.

18. The system according to claim 16, wherein the control unit is configured to tune and improve the linear set of equations describing either torque and force, or alternately field orientation and force, resulting from current flowing through the coils, based on feedback from the associated magnetic field sensors.

* * * * *